(12) United States Patent
Goossens et al.

(10) Patent No.: US 8,865,931 B2
(45) Date of Patent: Oct. 21, 2014

(54) TRANSESTERIFICATION PROCESS USING MIXED SALT ACETYLACETONATES CATALYSTS

(75) Inventors: Thomas Peter Anne Goossens, Ostend (BE); Freek Annie Camiel Vrielynck, Beernem (BE); Noel Gabriel Cornelius Hosten, Bruges (BE); Koen Jeanne Alfons Van Aken, Kuume (BE)

(73) Assignee: Ecosynth bvba, Ostend (BE)

( * ) Notice: Subject to any disclaimer, the term of this patent is extended or adjusted under 35 U.S.C. 154(b) by 0 days.

(21) Appl. No.: 13/704,057

(22) PCT Filed: Jun. 10, 2011

(86) PCT No.: PCT/EP2011/059672
§ 371 (c)(1),
(2), (4) Date: Dec. 13, 2012

(87) PCT Pub. No.: WO2011/157645
PCT Pub. Date: Dec. 22, 2011

(65) Prior Publication Data
US 2013/0090492 A1 Apr. 11, 2013

(30) Foreign Application Priority Data
Jun. 15, 2010 (GB) .................................. 1009969.5

(51) Int. Cl.
| | | |
|---|---|---|
| *C07C 67/02* | (2006.01) | |
| *B01J 31/26* | (2006.01) | |
| *C07C 68/06* | (2006.01) | |
| *C07C 67/03* | (2006.01) | |
| *B01J 31/22* | (2006.01) | |

(52) U.S. Cl.
CPC ............... *C07C 67/03* (2013.01); *G07C 67/28* (2013.01); *B01J 2531/842* (2013.01); *B01J 31/26* (2013.01); *C07C 68/06* (2013.01); *B01J 2531/26* (2013.01); *B01J 31/2234* (2013.01); *B01J 2231/49* (2013.01)
USPC ........................................................ 560/234

(58) Field of Classification Search
None
See application file for complete search history.

(56) References Cited

U.S. PATENT DOCUMENTS

| | | |
|---|---|---|
| 2,845,451 A | 7/1958 | Lautenschlager et al. |
| 3,528,945 A | 9/1970 | Stewart et al. |
| 3,528,946 A | 9/1970 | Stewart et al. |
| 3,532,671 A | 10/1970 | Carlson et al. |
| 4,202,990 A | 5/1980 | Murakami et al. |
| 4,777,265 A | 10/1988 | Merger et al. |
| 5,037,978 A | 8/1991 | Mirabelli |
| 5,481,024 A | 1/1996 | Hertenstein et al. |
| 5,610,313 A | 3/1997 | Riondel et al. |
| 5,840,957 A | 11/1998 | Kurian et al. |
| 5,856,611 A | 1/1999 | Schlaefer et al. |
| 6,222,063 B1 | 4/2001 | Zimmermann et al. |
| 6,350,895 B1 | 2/2002 | Kurian |
| 7,060,778 B2 | 6/2006 | Hofacker |
| 7,071,351 B2 | 7/2006 | Schmitt et al. |
| 2004/0249191 A1 | 12/2004 | Schmitt et al. |
| 2005/0006539 A1 | 1/2005 | Fischer et al. |
| 2006/0052572 A1 | 3/2006 | Hofacker |

FOREIGN PATENT DOCUMENTS

| | | |
|---|---|---|
| DE | 10008901 A1 | 9/2001 |
| DE | 102008043810 A1 | 5/2009 |
| EP | 0236994 A1 | 9/1987 |
| EP | 0317913 A2 | 5/1989 |
| EP | 0902017 A1 | 3/1999 |
| EP | 1064247 A1 | 1/2001 |
| FR | 2707290 A1 | 1/1995 |
| GB | 2072186 A | 9/1981 |
| JP | 53105417 A | 9/1978 |
| JP | 57183745 A | 11/1982 |
| JP | 2004010551 A | 1/2004 |
| JP | 20055132790 A | 5/2005 |
| WO | 2009003746 A1 | 1/2009 |
| WO | 2011027070 A1 | 3/2011 |

OTHER PUBLICATIONS

Anonymous: "Metal acetylacetonates", Wikipedia, Mar. 26, 2012, Retrieved from the Internet: URL:http://enwikipedia.org/wiki/Metal_acetylacetonates.
Database WPI, Week 8251, Thomson Scientific, London, GB; AN 1982-10253J; XP002681475.
International Preliminary Report on Patentability for International Application No. PCT/EP2011/059672 mailed Dec. 19, 2012.
International Search Report for International Application No. PCT/EP2011/059672 mailed Sep. 3, 2012.

*Primary Examiner* — Brandon Fetterolf
*Assistant Examiner* — Ana Z Muresan
(74) *Attorney, Agent, or Firm* — Dinsmore & Shohl LLP

(57) ABSTRACT

This invention is directed to a process for the production of a variety of esters, particularly acrylate and methacrylate-based esters, by a transesterification reaction. This objective is achieved by reaction of an ester of a carboxylic or a carbonic acid, in particular of a saturated or unsaturated, typically, a 3 to 4 carbon atom carboxylic acid; with an alcohol in the presence of a catalyst comprising the combination of a metal 1,3-dicarbonyl complex (pref. Zn or Fe acetylacetonate) and a salt, in particular an inorganic salt, pref. ZnCl2, LiCI, NaCI, NH4CI or Lil. These catalysts are prepared from readily available starting materials within the reaction medium without the need for isolation (in-situ preparation).

10 Claims, No Drawings

TRANSESTERIFICATION PROCESS USING MIXED SALT ACETYLACETONATES CATALYSTS

FIELD OF THE INVENTION

This invention relates to an improved process for the production of carboxylic esters, polyesters and carbonic esters, particularly carboxylic esters containing other functional groups, by a catalytic transesterification reaction. In particular, the invention relates to an improved process for production of acrylate and methacrylate esters using a mixture of a metal 1,3-dicarbonyl chelate and a salt, as catalysts in the transesterification reaction.

BACKGROUND OF THE INVENTION

Transesterification is an important process in the exchange of organic residues in several industrial processes. It is for example used in the large scale synthesis of polyesters. In this application diesters undergo transesterification with diols to form macromolecules. Another example is in the production of biodiesel (fatty acid methyl ester, FAME) through transesterification of vegetable oils or animal fats with short-chain aliphatic alcohols (typically methanol or ethanol). But also in other industrial processes such as (i) intramolecular transesterications leading to lactones and macrocycles, (ii) production of (intermediates of) specific active pharmaceutical ingredients (API's), (iii) production of polylactic acid (PLA) from lactide, (iv) co-synthesis of dimethyl carbonate and ethylene glycol from ethylene carbonate and methanol, transesterification is a crucial step.

Transesterification reactions normally are carried out in the presence of a catalyst, including among others mineral acids, metal hydroxides, metal oxides, metal alkoxides (aluminum isopropoxide, tetraalkoxytitanium, organotin alkoxides etc.), non-ionic bases (amines, dimethylaminopyridine, guanidines etc.) and lipase enzymes. (J. Otera and J. Nishikido, Esterification, p. 52-99, Wiley 2010). Activity of these conventional catalysts however is possibly hampered in the presence of unsaturated bonds, amines, additional hydroxy groups or other functional groups in the respective ester or alcohol reactants. A strong mineral acid such as sulfuric acid or methane sulfonic acid, for example, usually leads to slow reaction rates and the resulting transester product is typically accompanied by the formation of high concentrations of side-products. The latter usually result from dehydration of the alcohols to yield olefins and ethers which eventually contaminate the product. In case of acrylic esters, also Michael-addition products (addition of alcohol to C=C double bond) and substantial amounts of polymeric products are found in the final reaction mixture.

Similar to acid catalysts, alkali metal alkoxide catalysts (for example, sodium methoxide or potassium tert-butoxide) promote undesirable side reactions and, moreover, they are deactivated by the presence of water in the reaction solution. Therefore, catalyst should by continuously added to the reaction mixture, while it must subsequently be removed to avoid alkoxide-promoted polymerization or degradation during distillation or other thermal treatment of the products, especially if the products are unsaturated esters such as acrylic esters.

Titanium (Ti) and tin alkoxides generally have higher selectivity but suffer from specific drawbacks. Titanate catalysts are particularly sensitive to water (generally losing activity in mixtures containing greater than 500 ppm water), thus necessitating the same need to add more catalyst to the reaction. In addition, Ti compounds can lead to undesired discoloration (yellowing) during storage of the resulting product, which is caused by factors including the presence of Ti(III) compounds in addition to Ti(IV) compounds and/or by the tendency of titanium to form complexes. It is also recognized that tin compounds are potential carcinogens to humans, hence their presence in the final products is undesired. Rigorous removal is thus essential and residues should be efficiently disposed of.

Because of these problems with conventional catalysts, the need exists for an improved transesterification catalyst of high activity and selectivity in presence of other functional groups and with reduced sensitivity to water.

Previous steps toward meeting this need have been undertaken in the art by using metal acetylacetonates catalysts for the production of a variety of ester compounds. Examples of esters thus prepared include (meth)acrylic esters (U.S. Pat. No. 4,202,990, U.S. Pat. No. 7,071,351, US2004/0249191) or more specific allyl methacrylate (WO2009003746), prenyl (meth)acrylates esters (DE102008043810), ethylthioethanyl methacrylates (FR2707290). Also the production of aliphatic oligocarbonate polyols (U.S. Pat. No. 7,060,778, US2006/0052572, U.S. Pat. No. 6,350,895), alpha-ketocarboxylic esters (U.S. Pat. No. 6,222,063), wax monomers (U.S. Pat. No. 5,856,611), bis(3-hydroxypropyl)terephthalate monomer (U.S. Pat. No. 5,840,957), and polyethylene terephthalate resin (U.S. Pat. No. 3,528,946, U.S. Pat. No. 3,528,945) have been described.

The preferred metal is predominantly zirconium (U.S. Pat. No. 4,202,990, WO2009003746, U.S. Pat. No. 7,071,351, US2004/0249191, U.S. Pat. No. 5,856,611, FR2707290), but also other metal such as ytterbium(III) (U.S. Pat. No. 7,060,778, US2005/006539), yttrium/samarium compounds (U.S. Pat. No. 6,350,895), lanthanum (U.S. Pat. No. 5,840,957, EP1064247), hafnium (IV) (U.S. Pat. No. 5,037,978), cerium and lead (U.S. Pat. No. 3,532,671) have been described.

The use of Zn (II) or Fe (III) acetylacetonates is only occasionally mentioned. An example is the method for producing 2-methyl-2-hydroxy-1-propyl(meth)acrylate by reacting a (meth)acrylate with 2-methyl-2-hydroxy-1-propyl alcohol in the presence of a Zn-acetylacetonate catalyst (JP2005/132790). The yield was high (95%) while other frequently used catalysts such as tetra isopropoxy titanate gave lower yield (57%). Other examples include the manufacturing of dialkylaminoalkyl(meth)acrylates (JP 02017155) and the preparation of higher alkyl(meth)acrcylate esters starting from the lower alkyl esters (JP 53105417, EP 236994). Fe(III) acetylacetonate is described in synthesis of biodegradable glycolide/L-lactide copolymers (Polymer (2002), 43(9), 2595-2601)

We have found that the combination of a Zn or Fe 1,3-dicarbonyl complex and an inorganic salt shows an unexpectedly high activity. Thus, it is possible to achieve a higher conversion rate of transesterified ester products of a lower alkyl ester with an appropriate alcohol in the presence of mixture of salts consisting of a metal 1,3-dicarbonyl complex, in particular a Zn or Fe 1,3-dicarbonyl complex, more in particular a Zn (II) or Fe (III) 1,3-dicarbonyl complex and an inorganic salt.

SUMMARY OF THE INVENTION

This invention is directed to a general catalyst of high activity and selectivity for the production of a variety of esters, particularly acrylate and methacrylate-based esters, by a transesterification reaction. This objective is achieved by reacting an ester of a carboxylic or a carbonic acid, in particular of a saturated or unsaturated, typically, a 3 to 4 carbon atom carboxylic acid; with an alcohol in the presence of a catalyst consisting of a metal 1,3-dicarbonyl complex, more in particular a Zn (II) or Fe (III) 1,3-dicarbonyl complex and a salt, in particular an inorganic salt. These catalysts are prepared from readily available starting materials within the reaction medium (in situ preparation). Compared to and different from the currently available catalysts, there is no need to have the catalysts prepared in advance and isolated prior to its application in the actual transesterification reaction. Also, after reaction, the catalysts can be removed by either filtration or separation techniques making use of the ionic properties of the catalysts. In addition to the enhanced catalytic activity of the aforementioned combination, this ability of in situ preparation of the catalyst and convenient separation, adds to the commercial benefits of the present invention.

DETAILED DESCRIPTION OF THE INVENTION

As already mentioned hereinbefore, the present invention is directed to a process for the transesterification of an ester of a carboxylic or a carbonic acid, using an alcohol in the presence of a catalyst consisting of a metal 1,3-dicarbonyl complex and a salt.

When using carboxylic acid esters as starting materials, the transesterification process can generally be presented by the following reaction (Scheme 1).

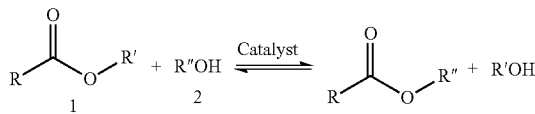

Scheme 1

In the aforementioned reaction scheme the carboxylic acid ester starting material is represented by the formula RCOOR' and can be an alkyl, cycloalkyl, aryl, aralkyl or alkaryl ester of a saturated or unsaturated aliphatic or aromatic carboxylic acid, where R is the saturated or unsaturated aliphatic or aromatic residue of said carboxylic acid and wherein R' is an alkyl, cycloalkyl, aryl, aralkyl or alkaryl; or wherein R and R' taken together with the atoms to which they are attached are part of a ring, such as for example lactide used in the production via ring opening polymerization (ROP) of poly(lactic acid (PLA)). As such, suitable carboxylic acid esters which may be employed in the transesterification reaction of the present invention will include alkyl, cycloalkyl, unsaturated aliphatic, cycloaliphatic and aryl esters. Examples of the alkyl esters include methyl formate, ethyl formate, propyl formate, butyl formate, amyl formate, hexyl formate, heptyl formate, octyl formate, nonyl formate, decyl formate, methyl acetate, ethyl acetate, propyl acetate, butyl acetate, amyl acetate, hexyl acetate, heptyl acetate, octyl acetate, nonyl acetate, decyl acetate, methyl propionate, ethyl propionate, propyl propionate, butyl propionate, amyl propionate, hexyl propionate, heptyl propionate, octyl propionate, nonyl propionate, decyl propionate, methyl butyrate, ethyl butyrate, propyl butyrate, butyl butyrate, amyl butyrate, hexyl butyrate, heptyl butyrate, octyl butyrate, nonyl butyrate, decyl butyrate, etc.; cycloalkyl esters such as cyclopentyl formate, cyclohexyl formate, cycloheptyl formate, cyclooctyl formate, cyclopentyl acetate, cyclohexyl acetate, cycloheptyl acetate, cyclooctyl acetate, cyclopentyl propionate, cyclohexyl propionate, cycloheptyl propionate, cyclooctyl propionate, cyclopentyl butyrate, cyclohexyl butyrate, cycloheptyl butyrate, cyclooctyl butyrate, etc.; unsaturated aliphatic esters such as vinyl formate, allyl formate, methallyl formate, crotonyl formate, vinyl acetate, allyl acetate, methallyl acetate, crotonyl acetate, vinyl propionate, allyl propionate, methallyl propionate, crotonyl propionate, vinyl butyrate, allyl butyrate, methallyl butyrate, crotonyl butyrate, etc.; unsaturated esters such as methyl acrylate, methyl crotonate, methyl oleate, allyl acrylate, etc.; cycloalkenyl esters such as cyclopentenyl formate, cyclohexenyl formate, cycloheptenyl formate, cyclooctenyl formate, cyclopentenyl acetate, cyclohexenyl acetate, cycloheptenyl acetate, cyclooctenyl acetate, cyclopentenyl propionate, cyclohexenyl propionate, cycloheptenyl propionate, cyclooctenyl propionate, cyclopentenyl butyrate, cyclohexenyl butyrate, cycloheptenyl butyrate, cyclooctenyl butyrate, etc.; aryl esters such as benzyl formate, benzyl acetate, benzyl propionate, benzyl butyrate, benzyl benzoate, etc. It is to be understood that, the esters herein listed are only representative of the class of esters, which may be employed, and that the present invention is not necessarily limited thereto.

When using a carbonic ester as starting materials, the transesterification process can generally be presented by the following reaction (Scheme 2)

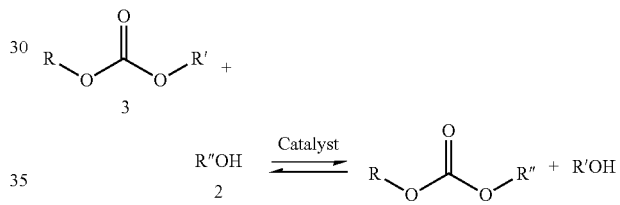

Scheme 2

The carbonic acid ester starting material is represented by the formula ROCOOR' and can be an alkyl, aralkyl (or a divalent group corresponding to these e.g. alkylene) ester of carbonic acid, where R and R' are each independently alkyl, cycloalkyl, aryl, aralkyl or alkaryl. Examples of the carbonic acid esters that can be used in the transesterification reaction of the present invention will include, but are not limited to ethylene carbonate, diethyl carbonate, propylene carbonate and dimethyl carbonate.

In both of the aforementioned reaction schemes, a suitable starting alcohol is represented by the formula R"OH, where R" is alkyl (i.e. refers to a linear or branched chain saturated acyclic hydrocarbon monovalent group optionally substituted with one or more substituents independently selected from the group consisting of hydroxy, amino, halo such as fluorinated and perfluorinated alcohols, alkenyl, mono- or di-alkyl-amino, sulfonate group, tetraalkyl ammonium, cyano, alkylthio, and heterocycles including saturated, unsaturated and partially saturated heterocycles such as morpholino or furan) or cycloalkyl (i.e. a monocyclic or polycyclic saturated ring comprising carbon and hydrogen atoms). Examples of cycloalkyl groups include, but are not limited to, $(C_3-C_7)$cycloalkyl groups, such as cyclopropyl, cyclobutyl, cyclopentyl, cyclohexyl, and cycloheptyl, and saturated cyclic and bicyclic terpenes. A cycloalkyl group can be unsubstituted or substituted by one, two or more suitable substituents. Preferably, the cycloalkyl group is a monocyclic ring or bicyclic ring, for example lower alkyl and cyclo lower alkyl containing from 3 to 20 carbon atoms. In a further embodiment R" may also be alkoxyalkyl; alkylpolyalkoxyalkyl; alkylphenoxyalkyl; alkylpolyphenoxyalkyl; phenylalkyl; alkylphenylalkyl; alkylmorpholinoalkyl; alkylpiperidinoalkyl; haloalkyl; cyanoalkyl; alkylthioalkyl; alkylimidazolidinones; mono- or di-alkyl-aminoalkyl, such as dimethylaminoethyl; oxazolidines; hydroxy alkyls such as hydroxyethyl, hydroxybutyl and the like, for example those derived from ethylene glycol (e.g. polyethylene glycol), butanediol, polyoxyethyleneols, and the like. In a particular embodiment R" is selected from the group consisting of alkyl; substituted alkyl (i.e. with one or more substituents independently selected from the group consisting of amino; halo such as fluorinated and perfluorinated alcohols; alkenyl; mono- or di-alkyl-amino, such as dimethyl-aminoethyl; sulfonate group; tetraalkyl ammonium; cyano; alkylthio; and heterocycles including saturated, unsaturated and partially saturated heterocycles such as morpholino, oxazolidine, imidazolidine or furan); cycloalkyl; alkoxyalkyl; alkylpolyalkoxyalkyl; alkylphenoxyalkyl; alkylpolyphenoxyalkyl; phenylalkyl; alkylphenylalkyl; alkylmorpholinoalkyl; alkylpiperidinoalkyl; hydroxy alkyls such as hydroxyethyl, hydroxybutyl and the like, for example those derived from ethylene glycol (e.g. polyethylene glycol), butanediol, polyoxyethyleneols, and the like. In a more particular embodiment R" is selected from the group consisting of alkyl; cycloalkyl; alkoxyalkyl; alkylpolyalkoxyalkyl; alkylphenoxyalkyl; alkylpolyphenoxyalkyl; phenylalkyl; alkylphenylalkyl; alkylmorpholinoalkyl; alkylpiperidinoalkyl; haloalkyl; cyanoalkyl; alkylthioalkyl; alkylimidazolidinones; mono- or di-alkyl-aminoalkyl, such as dimethyl-aminoethyl; alkyl oxazolidines; hydroxy alkyls such as hydroxyethyl, hydroxybutyl and the like, for example those derived from ethylene glycol (e.g. polyethylene glycol) butanediol, polyoxyethyleneols, and the like.

Preferred are those alcohols wherein the alkyl portions described in the above compounds are lower alkyl having from 2 to 20 carbon atoms. Examples of alcohols include butanol, pentanol, isodecyl, lauryl, cetyl, stearyl, alkyl ether of polyoxyethylene, dimethylaminoethanol, 2-N-oxazolidinyl)ethyl, 2-(N-morpholino)ethyl, dicyclopentenyloxyethyl, and the like.

The general requirements for the suitability of the alcohol for the transesterification reaction are that it is of higher normal boiling point than the lower alkyl alcohol being replaced (R'OH) and that it is stable to the relatively mild conditions of the reaction. Alcohols containing relatively high water contents (>1000 ppm) are dehydrated by conventional methods before use, e.g. by azeotropic dehydration, although the catalysts of this invention are found to readily tolerate alcohol water levels of 200-500 ppm with no significant decrease in activity, which is in contrast to many other catalysts in the art.

The catalyst of the present invention consists of a mixture of metal acetylacetonates represented by the following general formula (I) and a salt $M'^{m+}[X^{p-}]_n$

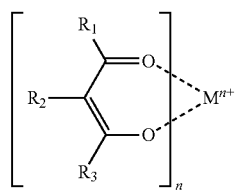

Formula I where n=1, 2, 3 or 4 and $R^1$ and $R^3$ are each independently $C_1$-$C_4$ alkyl or phenyl, $R^2$ is hydrogen, $C_1$-$C_4$ alkyl, phenyl or substituted phenyl such as p-methylphenyl, p-hydroxyphenyl, and the like. Suitable chelate compounds of the metal include for example the acetylacetonate, 2,4-hexanedionate, 3,5-heptanedionate, 3-phenylacetoacetonate, 2,2,6,6-tetramethyl-3,5-heptanedionate, or 1,3-diphenylacetonate.

M can be aluminum, alkali and earth alkali metals such as lithium, sodium, potassium, magnesium, barium and calcium, or transition metals such as indium, tin, scandium, yttrium, lanthanum, hafnium, titanium, zirconium, chromium, manganese, cobalt, nickel, copper, zinc or iron. Preferred members of this group are zinc acetylacetonate (Zn $(acac)_2$) and Iron (III) acetylacetonate (Fe$(acac)_3$).

The salt $M'^{m+}[X^{p-}]_n$, can contain any inorganic or organic cation, i.e. $M'^{m+}$ having $m^+$ as a charge (i.e. m an integer between 1 and 6), preferably $Zn^{2+}$, $Li^+$, $Na^+$, $NH_4^+$; and any inorganic or organic anion, i.e. $X^{p-}$ having $p^-$ as a charge (i.e. p an integer between 1 and 6), such as halide, carbonate $(CO_3^{2-})$, hydrogencarbonate $(HCO_3^-)$, phosphate $(PO_4^{3-})$, hydrogen phosphate $(HPO_4^{2-})$, dihydrogen phosphate $(H_2PO_4^-)$, sulfate $(SO_4^{2-})$, sulfite $(SO_3^{2-})$ and carboxylates; and wherein n represents the number of anions needed to match the charge of the cation. Preferred anions are halides such as $Cl^-$, $Br^-$ and $I^-$. Preferred members of the salts $M'^{m+}$ $X^{p-}$ are $ZnCl_2$, LiCl, NaCl, $NH_4Cl$, LiI.

The mol ratio of metal acetylacetonate and salt generally is from 1:1 to 10:1, and preferably from 2:1 to 1:2.

The catalysts may be prepared in-situ in transesterification mixtures or solutions by mixing the appropriate acetylacetonate salt with inorganic salts. It is a key aspect of this invention that the single salts which are used in the preparation of the catalyst were less effective in transesterification catalysis.

The catalysts of this invention are used in amounts of from about 0.01 to about 5.0 mol % based on the initial charge of alcohol, in particular from about 1.0 to about 5.0 mol %; more in particular about 1.25 mol %, about Larger amounts of catalyst may be used but are not usually necessary. The catalyst typically is present at the beginning of reactant combination and remains present throughout the reaction period.

In the case of the production of (meth)acrylic esters, the starting (meth)acrylic ester may be used as an azeotroping solvent to facilitate removal of the product alcohol and to drive the reaction to completion. Other suitable solvents such as hexane, cyclohexane, heptane, toluene also may be used for these purposes.

The initial mole ratio of saturated, aromatic, or unsaturated (for example, (meth)acrylic) ester to alcohol generally is from 1:1 to 10:1, and is preferably 2:1 to 5:1.

The reaction is carried out under atmospheric or reduced pressure conditions. Suitable reaction temperatures range from about 20° C. to about 140° C., more typically from about 80° C. to about 120° C.

The reaction can be run in organic solvents or their mixtures or without addition of solvents. Suitable organic solvents are for example tertiary alcohols, preferred tert-butanol, tert-amyl alcohol, pyridine, poly-$C_1$-$C_4$-alkyleneglycol-$C_1$-$C_4$-alkylethers, preferably 1,2-dimethoxyethane, diethylene glycol dimethylether, polyethylene glycol dimethylether 500, $C_1$-$C_4$-alkylencarbonates, in particular propylene carbonate, $C_3$-$C_6$-alkyl acetic acids, in particular tert-butylacetic acid, THF, toluene, 1,3-dioxane, acetone, iso-butylmethylketone, ethylmethylketone, 1,4-dioxane, tert-butyl methyl ether, cyclohexane, methylcyclohexane, toluene, hexane, dimethoxymethane, 1,1-dimethoxyethane, acetonitrile, in homogeneous as well as in multiphase mixtures.

The starting materials normally are brought to reflux in the presence of the catalyst while the product alcohol is azeotroped from the system, facilitated by excess of the starting ester.

The starting materials are present either dissolved, suspended as solids or in emulsion in the reaction medium.

The reaction can take place continuous, for example in a tubular reactor or in a reactor cascade, or discontinuous.

The conversion can take place in all for such a conversion suitable reactors. Such reactors are known to the person skilled in the art. Preferred ones are a stirred tank reactors.

For the mixing of the reaction, the common methods can be used. Particular stirrers are not required. The mixing can take place for example via feeding a gas, such as for example an oxygen containing gas, which is preferably used. The reaction medium can be in a single phase or multiphase and the reactants can be dissolved, suspended or emulsified.

The temperature is set during the reaction on the desired value and can, if desired, during the reaction process be increased or reduced.

The reaction time of transesterification using the catalysts according to the invention is usually 30 min to 24 hours, preferably between 1 hour and 12 hours.

On completion of the reaction the catalyst may be removed, if desired, from the product by applying filtration, electrical filtration, absorption, centrifugation decanting or treating the product mixture with activated carbon, neutral alumina, silica, silica/alumina, and the like.

However, and as already mentioned in the summary of the invention hereinbefore, there is no need to remove the catalyst from the reaction medium as its presence has no detrimental effect on the final transesterification products and is unlikely to interfere with post processing steps like a subsequent polymerization of unsaturated products or in many other applications of saturated, aromatic, or unsaturated products.

If the catalysts are removed from the reaction medium, this can simply be achieved for example by filtration or evaporation of the reaction product (the catalyst, i.e. the salt complex remains), they can be used in subsequent runs without significant loss of activity.

As such the catalyst complex of the present invention complies with the capabilities that are usually required from a catalyst candidate:

- the catalyst should exhibit high activity, i.e. actively and efficiently promote the transesterification reaction within a limited period of time. As is evident from the exemplary part hereinafter, the catalyst complex of the present invention has a dramatic impact on the conversion rate of the transesterification;
- the catalyst should exhibit high selectivity. Again and apparent from the exemplary part hereinafter, the catalyst complex of the present invention, result in high transesterification yields;
- the catalyst should exhibit sufficient stability under the prevailing operating conditions to be capable of recycling and re-using in the transesterification reaction without losing its activity and selectivity. As extensively described herein, the catalyst complex of the present invention can easily be re-cycled from the reaction medium without significant loss in activity; and
- the catalyst should also be inexpensive to produce. Given the possibility of in situ preparation of the catalyst in the reaction mixture without the need to remove eventual reagent residues and further reaction products from the reaction medium during the transesterification reaction, the catalysts of the present invention will be cheaper in operation (no pre-synthesis and isolation is required).

The reaction conditions for transesterification according this invention are mild. Due to the low temperatures and other mild conditions, the formation of byproducts due to undesirable radical polymerization when using (meth)acrylates, are suppressed. This polymerization can otherwise only be prevented by addition of a significant amount of radical inhibitors. Examples of such radical inhibitors include hydroquinone, hydroquinone monomethylether, phenothiazine, diethylhydroxylamine, phenols such as 2-tert-butyl-4-methylphenol, 6-tert-butyl-2,4-dimethylphenol, catechols such as di-tert-butylcatechol, TEMPO derivatives such as 4-hydroxy-2,2,6,6-tetramethyl-piperidin N-oxyl, or 4-oxo-2,2,6,6-tetramethyl-piperidin N-oxyl. These inhibitors are usually used in amounts from 50 to 2000 ppm. In addition, oxygen also may be found beneficial in inhibiting polymerization in the presence of inhibitors and is introduced into the reaction system, often in the form of an oxygen containing gas, preferably air, in amounts such that the gas phase above the reaction mixture remains below the explosion limit.

In the case of acrylic esters, the end product of the transesterification reactions find applications as monomers or co-monomers in the preparation of dispersions, for example in acryl dispersions, as reactive solvents, for example in radiation-curable coatings or in colors, as well as in dispersions for application in the paper industry, in the cosmetic industry, in the pharma industry, in the agro industry, in the textile industry and in oil production.

In a further aspect the present invention provides the catalyst for use in the transesterification reaction of an ester of a carboxylic or a carbonic acid, said catalyst being characterized in that it consists of a the combination of a metal 1,3-dicarbonyl chelate and a salt.

In a particular embodiment and as already explained hereinbefore, the salt is preferably selected from the group consisting of $ZnCl_2$, LiCl, NaCl, $NH_4Cl$, and LiI; and the metal 1,3-dicarbonyl chelate in the aforementioned combination, is represented by the formula

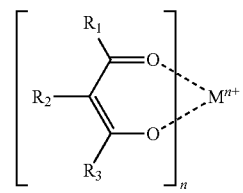

wherein n=1, 2, 3 or 4; $R^1$ is C1-C4 alkyl, phenyl or substituted phenyl; $R^2$ is hydrogen, C1-C4 alkyl, phenyl or substituted phenyl; $R^3$ is C1-C4 alkyl, phenyl or substituted phenyl; M represents a metal cation, typically selected from the group consisting of poor metals such as aluminium; alkali and earth alkali metals such as lithium, sodium, potassium, magnesium, barium and calcium; and transition metals such as indium, tin, scandium, yttrium, lanthanum, hafnium, titanium, zirconium, chromium, manganese, cobalt, nickel, copper, zinc or iron. In one particular embodiment of the present invention the salt is selected from LiCl, LiI, $ZnCl_2$ or $Cs_2CO_3$; more in particular LiCl, LiI, or $ZnCl_2$; and the metal 1,3-dicarbonyl chelate in the aforementioned combination, is represented by the formula

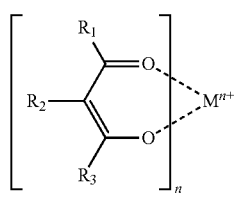

wherein n=1, 2, 3 or 4; $R^1$ is C1-C4 alkyl, phenyl or substituted phenyl; $R^2$ is hydrogen, C1-C4 alkyl, phenyl or substituted phenyl; $R^3$ is C1-C4 alkyl, phenyl or substituted phenyl; and wherein M represents a metal cation selected from zinc or iron; more in particular the metal 1,3-dicarbonyl chelate is characterized in that n is 1, 2, 3, or 4; $R^1$ and $R^3$ are each independently C1-C4 alkyl (preferably methyl); $R^2$ is hydrogen; and M represents a metal cation selected from zinc or iron. Even more in particular the metal 1,3-dicarbonyl chelate is selected from zinc acetylacetonate ($Zn(acac)_2$) or iron acetylacetonate ($Fe(acac)_3$).

Having described the invention in general terms, more specific examples are provided below for purposes of illustrating the present invention.

EXAMPLE 1

Effect of Mixed Salt on Typical Reaction (Neat)

A Corning tube is charged with 2 ml of ethyl acetate (20.47 mmol; 17 equivalents), 0.125 ml of benzyl alcohol (1.20 mmol; 1 equivalent) and a catalyst. The mixture is heated at 80° C. Samples are analyzed by gas chromatography. The results are summarized in Table 1.

TABLE 1

% of benzyl acetate formed at 80° C.

| Catalyst | mol % | 1 h | 3 h | 5 h |
| --- | --- | --- | --- | --- |
| $Zn(acac)_2$ | 5 | 2% | 6% | 13% |
| LiCl | 2.5 | 0% | 0% | 0% |
| $Zn(acac)_2$ | 5 | 28% | 53% | 62% |
| LiCl | 2.5 | | | |
| LiI | 2.5 | 1% | 2% | 2% |
| $Zn(acac)_2$ | 5 | 34% | 54% | 64% |
| LiI | 2.5 | | | |
| $Zn(acac)_2$ | 5 | 42% | 57% | 68% |
| $K_3PO_4$ | 2.5 | | | |
| $K_3PO_4$ | 2.5 | 16% | 27% | 37% |
| $Zn(acac)_2$ | 5 | 60% | 72% | 78% |
| $Cs_2CO_3$ | 2.5 | | | |
| $Cs_2CO_3$ | 2.5 | 16% | 35% | 50% |

EXAMPLE 2

Effect of Mixed Salt in a Solvent 0.216 ml of benzyl alcohol (2.09 mmol; 1 equivalent) and 0.204 ml of ethyl acetate (2.09 mmol; 1 equivalent) are dissolved in 2 ml of toluene (18.82 mmol; 9 equivalents). The mixture is heated at 80° C. in the presence of a catalyst. Samples are analyzed by gas chromatography. The results are summarized in Table 2.

TABLE 2

% of benzyl acetate formed at 80° C.

| Catalyst | mol % | 1 h | 3 h |
| --- | --- | --- | --- |
| $Zn(acac)_2$ | 5 | 10% | 35% |
| $ZnCl_2$ | 2.5 | 8% | 15% |
| $Zn(acac)_2$ | 5 | 35% | 50% |
| $ZnCl_2$ | 2.5 | | |

EXAMPLE 3

Effect of Mixed Zn and Fe acac Salt in the Reaction with Dimethyl Carbonate

In a Corning tube 2 ml of dimethyl carbonate (23.73 mmol; 17 equivalents), 0.144 ml of benzylalcohol (1.40 mmol; 1 equivalent) and a catalyst are mixed together. The mixture is heated with stirring to 80° C. The product distribution is analyzed by means of gas chromatography. The results obtained are listed in Table 3.

TABLE 3

% of benzyl methyl carbonate formed at 80° C.

| Catalyst | mol % | 1 h | 3 h | 6 h |
| --- | --- | --- | --- | --- |
| $Zn(acac)_2$ | 5 | 8% | 15% | 28% |
| LiCl | 5 | 0% | 0% | 0% |
| $Zn(acac)_2$ | 5 | 42% | 63% | 80% |
| LiCl | 5 | | | |
| LiI | 5 | 2% | 2% | 2% |
| $Zn(acac)_2$ | 5 | 57% | 81% | 93% |
| LiI | 5 | | | |
| $ZnCl_2$ | 5 | 5% | 11% | 18% |
| $Zn(acac)_2$ | 5 | 22% | 37% | 62% |
| $ZnCl_2$ | 5 | | | |
| $Fe(acac)_3$ | 5 | 35% | 54% | 76% |
| $Fe(acac)_3$ | 5% | 57% | 79% | 93% |
| LiI | 5% | | | |

EXAMPLE 4

Reaction of Benzylalcohol with Dimethyl Carbonate (Scale-Up)

A 500 ml flask was loaded with 160 g of dimethyl carbonate (1.78 moles), 48 g of benzylalcohol (0.44 moles), 5.9 g of zinc acetylacetonate (22.2 mmol) and 3 g of lithium iodide (22.2 mmol). The flask was equipped with an agitator, a thermometer and a fractional distillation column. The mixture was heated to reflux at atmospheric pressure while an azeotropic mixture of DMC and methanol was removed from the upper part of the fractionating column. The reaction was continued in this manner for three hours while the temperature at the top of the column was approximately 63° C. and the temperature of the oil bath was 130° C. The catalyst was recovered by vacuum filtration and excess DMC was removed under reduced pressure. GC-analysis showed full conversion of benzylalcohol to a mixture of two products: 78% of benzylmethyl carbonate and 22% of dibenzylcarbonate.

EXAMPLE 5

Reaction of Benzylalcohol with Dimethyl Carbonate (Scale-Up) with Recycled Catalyst To a 500 ml flask loaded with 160 g of fresh dimethyl carbonate and 48 g of fresh benzylalcohol was added the recovered catalyst from example 4, i.e. the combination of zinc acetylacetonate with lithium iodide. The flask was equipped with an agitator, a thermometer and a fractional distillation column. The mixture was heated to reflux at atmospheric pressure while an azeotropic mixture of DMC and methanol was removed from the upper part of the fractionating column. The reaction was continued in this manner for three hours while the temperature at the top of the column was approximately 63° C. and the temperature of the oil bath was 130° C. GC-analysis showed that the recycled catalyst had maintained its activity (Table 4).

TABLE 4

| Catalyst recycling: % DMC converted | | |
|---|---|---|
| Catalyst use # | 2 h | 3 h |
| First use | 94% | 100% |
| Second use | 95% | 100% |

EXAMPLE 6

Reaction of Prenol (a.k.a. Prenylalcohol) with Methyl Methacrylate

A mixture of methyl methacrylate (3 ml; 28.17 mmol; 5 equivalents) and prenol (0.572 ml; 5.63 mmol; 1 equivalent) is heated at 65° C. in the presence of 50 ppm phenothiazine, 500 ppm hydroquinone monomethyl ether and a catalyst. Gas chromatography was used to determine the conversion. Results are shown in Table 5.

TABLE 5

| | | Product formed (%) at 65° C. | | |
|---|---|---|---|---|
| Catalyst | mol % | 3 h | 5 h | 24 h |
| Zn(acac)$_2$ | 1.25 | 6% | 8% | 17% |
| LiCl | 1.25 | | | |
| Zn(acac)$_2$ | 1.25 | 22% | 31% | 58% |
| LiCl | 1.25 | | | |
| LiI | 1.25 | 0% | 0% | 0% |
| Zn(acac)$_2$ | 1.25 | 16% | 24% | 51% |
| LiI | 1.25 | | | |

EXAMPLE 7

Reaction of Prenol with Methyl Methacrylate (Scale-Up)

188 g of methyl methacrylate (MMA; 1.88 moles), 35 g of prenol (0.40 moles), 1.24 g of zinc acetylacetonate (4.7 mmol), 0.2 g of LiCl (4.7 mmol), 0.9 g of phenothiazine (4.5 mmol) and 0.7 g of hydroquinone monomethyl ether (5.6 mmol) were added to a 500 ml flask equipped with an agitator, thermometer, and fractional distillation column. The mixture was heated at reflux under atmospheric pressure while an azeotropic mixture of MMA and methanol was removed at the top of the column. The reaction was completed after two hours. The temperature at the top of the column during the reaction was 65° C. while the temperature in the reaction vessel was 130° C. Excess MMA was removed under reduced pressure (100 mbar). The product was separated from the catalyst and inhibitors by vacuum distillation. 61 grams (99.0% yield) of a clear, colorless liquid was obtained. Gas-liquid chromatographic (GLC) analysis showed 99.7% conversion of prenol to prenyl methacrylate of 95% purity.

EXAMPLE 8

Reaction of Prenol with Methyl Acrylate

A mixture of methyl acrylate (2 ml; 22.22 mmol; 5 equivalents) and prenol (0.451 ml; 4.44 mmol; 1 equivalent) is heated at 65° C. in the presence of phenothiazine (8.8 mg; 1 mol %), hydroquinone monomethyl ether (8.3 mg; 1.5 mol %) and a catalyst. Gas chromatography was used to determine the conversion. Results are shown in Table 6.

TABLE 6

| | | Product formed (%) at 65° C. | | |
|---|---|---|---|---|
| Catalyst | mol % | 1 h | 4 h | 21 h |
| Zn(acac)$_2$ | 1.25 | 8% | 16% | 70% |
| LiCl | 1.25 | 0% | 0% | 0% |
| Zn(acac)$_2$ | 1.25 | 46% | 62% | 86% |
| LiCl | 1.25 | | | |
| LiI | 1.25 | 0% | 0% | 0% |
| Zn(acac)$_2$ | 1.25 | 30% | 42% | 72% |
| LiI | 1.25 | | | |
| ZnCl$_2$ | 1.25 | 0% | 0% | 0% |
| Zn(acac)$_2$ | 1.25 | 14% | 29% | 90% |
| ZnCl$_2$ | 1.25 | | | |
| Fe(acac)$_3$ | 1.25 | 15% | 38% | 69% |
| Fe(acac)$_3$ | 1.25 | 23% | 47% | 78% |
| LiI | 1.25 | | | |

EXAMPLE 9

Reaction of Methyl Benzoate with 1-butanol

The preparation of butyl benzoate was performed by adding 216 g of methyl benzoate (1.59 mol), 132 g of n-butanol (1.78 mol), 21 g of zinc acetylacetonate (0.08 mol), 5.4 g of ZnCl$_2$ (0.04 mol) and 100 ml of cyclohexane to a 1 liter flask equipped with an agitator, thermometer, fractional distillation column and a Dean and Stark trap. The solution was heated to atmospheric reflux while an azeotropic mixture of cyclohexane and methanol was removed at the top of the column. The reaction was continued in this manner for approximately 7 hours. Analysis of the reaction mixture showed 94% conversion of methyl benzoate to butyl benzoate.

EXAMPLE 10

Reaction of Dimethyl Terephthalate with 1,3-propanediol

A 250 ml flask equipped with a stirrer and distillation column was charged with 58.5 g of dimethyl terephthalate (DMT) and 45.7 g of 1,3-propanediol for a mole ratio of 1,3-propanediol:DMT of 2:1. The flask was then purged with nitrogen and the contents of the flask were heated. When the temperature inside the flask reached about 150° C. and all of the DMT had melted 4 g of anhydrous zinc acetylacetonate and 0.3 g of lithium chloride was added. Upon addition of the catalyst, methanol evolved. The methanol was removed by distillation. The temperature was held at 150° C. and the amount of methanol collected was taken as a measure for the progress of the reaction. The cumulative amount of methanol collected versus time is shown in Table 7. A total of 23.5 ml of methanol was collected in 80 minutes. The theoretical amount of methanol for complete transesterification is 24.4 ml. Some methanol may have remained in the reaction mixture and been removed upon application of vacuum during polycondensation.

TABLE 7

Methanol evolution versus time

| Time (minutes) | MeOH (ml) |
|---|---|
| 0 | 0 |
| 5 | 10 |
| 8 | 15 |
| 17 | 18 |
| 25 | 20 |
| 35 | 21 |
| 46 | 22 |
| 60 | 23 |
| 80 | 23.5 |

EXAMPLE 11

Reaction of Methyl Methacrylate with 1-decanol

To a 1 liter flask equipped with an agitator, thermometer and a Vigreux fractionating column were added 188 g (1.88 mol) of methyl methacrylate (MMA), 59.4 g (0.376 mol) of n-decyl alcohol, 1.25 mol % of zinc acetylacetonate, 1.25 mol % of LiCl and 0.75 g of phenothiazine, and 0.62 g of hydroquinone free radical polymerization inhibitor. The mixture was heated to reflux at atmospheric pressure while an azeotropic mixture of MMA and methanol was removed from the upper part of the fractionation column. The reaction was continued in this manner for approximately five hours. After vacuum filtration of the catalyst and inhibitors, the excess of MMA was removed under vacuum and the resulting n-decyl methacrylate (DMA) was isolated (84.3 grams, 99.1% yield) and analyzed. Gas-liquid chromatographic (GLC) analysis showed 99% conversion of 1-decanol to DMA of 98% purity.

EXAMPLE 12

Reaction of Methyl Methacrylate with 1-decanol with Recycled Catalyst

To a 1 liter flask equipped with an agitator, thermometer and a Vigreux fractionating column were added 188 g of fresh MMA, 59.4 g of fresh 1-decanol, and the recovered catalyst and inhibitors of example 11. The mixture was heated to reflux at atmospheric pressure while an azeotropic mixture of MMA and methanol was removed from the upper part of the fractionation column. The reaction was continued in this manner for approximately five hours. GC-analysis showed full conversion of 1-decanol to DMA which demonstrates that the recycled catalyst was still active.

EXAMPLE 13

Reaction of Methyl Laurate with Butanol

A 500 ml flask equipped with a stirrer and distillation column was charged with 62.5 g (0.29 mol) of methyl laurate, 162 g (2.19 mol) of n-butanol, 3.8 g (15 mmol) of Zn(acac)$_2$ and 1 g (7.5 mmol) of LiI. The mixture was heated to reflux at atmospheric pressure while methanol was removed from the upper part of the column. The temperature of the oil bath was kept at 130° C. and the reaction was continued in this manner for five hours. On completion of the reaction, excess butanol was distilled off and a clear, yellow oil was obtained. Gas-liquid chromatographic analysis showed full conversion of methyl laurate to butyl laurate.

EXAMPLE 14

Reaction of 2-ethyl-1,3-hexanediol with Ethyl Acetate to Demonstrate the Selectivity Primary and Secondary Alcohol (Scheme 3)

Seventeen equivalents of ethylacetate (2.015 mL; 20.5 mmol) and one equivalent of 2-ethyl-1,3-hexanediol (0.185 mL; 1.2 mmol) were mixed in the presence of 5 mol % of Zn(acac)$_2$ (0.06 mmol) and 5 mol % of LiCl (0.06 mmol). The mixture was stirred in a sealed vial at 80° C. After 1, 4, 6 and 24 hours, a sample was taken from the reaction mixture for GC-analysis (Table 8).

Scheme 3

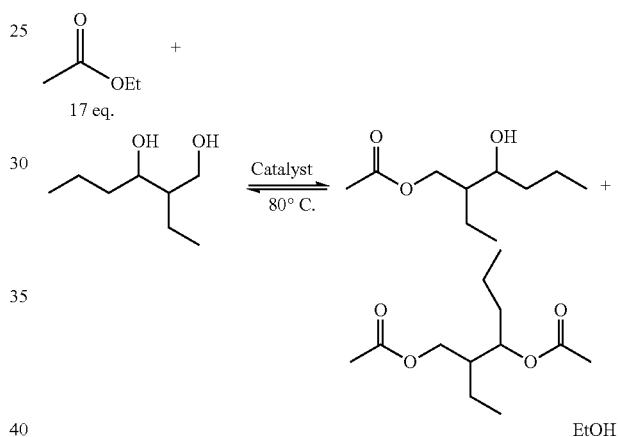

TABLE 8

| | | Product formed (%) at 80° C. | | | |
|---|---|---|---|---|---|
| Catalyst | mol % | 1 h | 4 h | 6 h | 24 h |
| LiCl | 5 | 0% | 0% | 0% | 0% |
| Zn(acac)$_2$ | 5 | 11% | 16% | 26% | 71% |
| Zn(acac)$_2$ LiCl | 5 5 | 47% | 60% | 74% | 93% |

As is evident from Table 9, using the catalyst of the present invention, there is a selective formation of the mono-ester practically without formation of the di-ester.

TABLE 9

| | | Ratio mono/di-ester (in %) at 80° C. | | | |
|---|---|---|---|---|---|
| Catalyst | mol % | 1 h | 4 h | 6 h | 24 h |
| LiCl | 5 | / | / | / | / |
| Zn(acac)$_2$ | 5 | / | / | / | 91-9 |
| Zn(acac)$_2$ LiCl | 5 5 | 96-4 | 94-6 | 90-10 | 77-23 |

EXAMPLE 15

Reaction of 3-methyl-1,3-butanediol with Ethyl Acetate to Demonstrate Selectivity of Primary Alcohol Over Tertiary Alcohol (Scheme 4)

Seventeen equivalents of ethylacetate (2.015 mL; 20.5 mmol) and one equivalent of 3-methyl-1,3-butanediol (0.130 mL; 1.2 mmol) were mixed in the presence of 5 mol % of Zn(acac)$_2$ (0.06 mmol) and 5 mol % of LiCl (0.06 mmol). The mixture was stirred in a sealed vial at 80° C. After 1, 4, 6 and 24 hours, a sample was taken from the reaction mixture for GC-analysis (Table 10).

Scheme 4

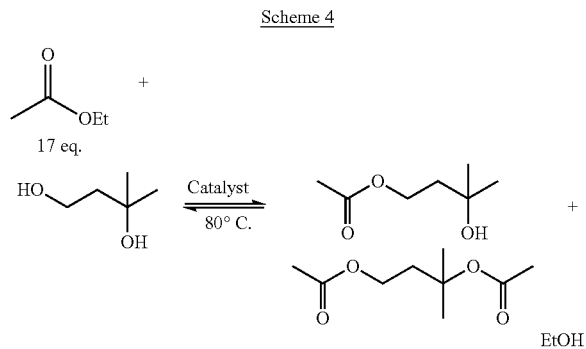

As is evident from Table 11, there is a selective formation of the mono-ester using the catalyst of the present invention, practically without formation of the di-ester.

TABLE 10

| | Product formed (%) at 80° C. | | | | |
|---|---|---|---|---|---|
| Catalyst | mol % | 1 h | 4 h | 6 h | 24 h |
| LiCl | 5 | 0% | 0% | 0% | 0% |
| Zn(acac)$_2$ | 5 | 15% | 22% | 36% | 75% |
| Zn(acac)$_2$ | 5 | 50% | 71% | 76% | 87% |
| LiCl | 5 | | | | |

TABLE 11

| | Ratio mono/di-ester (in %) at 80° C. | | | | |
|---|---|---|---|---|---|
| Catalyst | mol % | 1 h | 4 h | 6 h | 24 h |
| LiCl | 5 | / | / | / | / |
| Zn(acac)$_2$ | 5 | / | 100-0 | 100-0 | 100-0 |
| Zn(acac)$_2$ | 5 | 100-0 | 100-0 | 100-0 | >99-trace |
| LiCl | 5 | | | | |

EXAMPLE 16

Reaction of 2-methyl-2,4-pentanediol with Ethyl Acetate to Demonstrate Selectivity of Secondary Alcohol Over Tertiary Alcohol (Scheme 5)

Seventeen equivalents of ethylacetate (2.015 mL; 20.5 mmol) and one equivalent of 2-methyl-2,4-pentanediol (0.155 mL; 1.2 mmol) are mixed in the presence of 5 mol % of Zn(acac)$_2$ (0.06 mmol) and 5 mol % of LiCl (0.06 mmol). The mixture is stirred in a sealed vial at 80° C. After 1, 4, 6 and 24 hours, a sample is taken from the reaction mixture for GC-analysis (Table 12).

Scheme 5

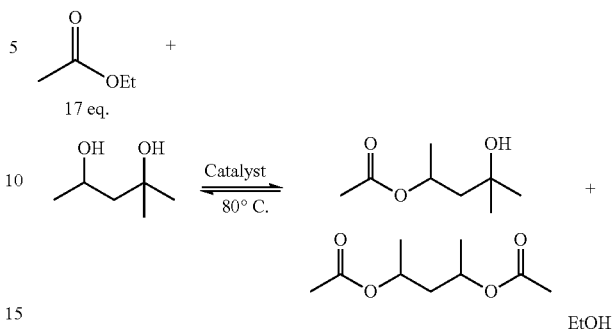

As is evident from Table 13, there is a selective formation of the mono-ester using the catalyst of the present invention practically without formation of the di-ester.

TABLE 12

| | Product formed (%) at 80° C. | | | | |
|---|---|---|---|---|---|
| Catalyst | mol % | 1 h | 4 h | 6 h | 24 h |
| LiCl | 5 | 0% | 0% | 0% | 0% |
| Zn(acac)$_2$ | 5 | 0% | 4% | 5% | 12% |
| Zn(acac)$_2$ | 5 | 3% | 7% | 9% | 15% |
| LiCl | 5 | | | | |

TABLE 13

| | Ratio mono/di-ester (in %) at 80° C. | | | | |
|---|---|---|---|---|---|
| Catalyst | mol % | 1 h | 4 h | 6 h | 24 h |
| LiCl | 5 | / | / | / | / |
| Zn(acac)$_2$ | 5 | / | 100-0 | 100-0 | 100-0 |
| Zn(acac)$_2$ | 5 | 100-0 | 100-0 | 100-0 | >99-trace |
| LiCl | 5 | | | | |

EXAMPLE 17

Reaction of ethyl(−)-L-lactate with Benzylalcohol to Demonstrate the Selectivity (Scheme 6)

One equivalent of ethyl(−)-L-lactate (1.140 mL; 0.001 mmol) and one equivalent of Benzylalcohol (1.035 mL; 0.001 mmol) are mixed in the presence of 5 mol % of Zn(acac)$_2$ (0.0005 mmol) and 5 mol % of LiCl (0.0005 mmol). The mixture is stirred in a sealed vial at 80° C. After 1, 4, 6 and 24 hours, a sample is taken from the reaction mixture for GC-analysis (Table 14).

Scheme 6

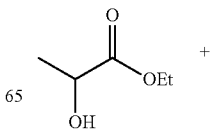

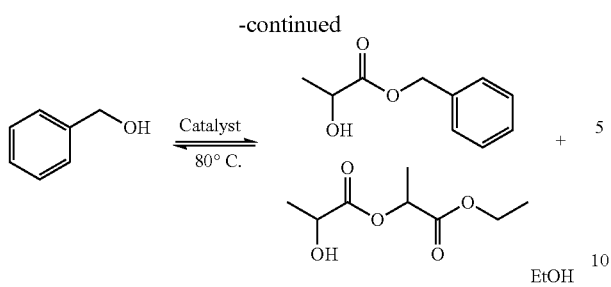

With these reagents, and using standard catalysts, one typically obtains formation of a significant fraction of the di-ester where the formation of the benzylester is desired. As is evident from Table 13, using the catalyst of the present invention, the selectivity in the formation of the benzylester is considerably enhanced.

TABLE 14

Ratio benzylester/di-ester (in %) at 80° C.

| Catalyst | mol % | 1 h | 4 h | 6 h | 24 h |
|---|---|---|---|---|---|
| LiCl | 5 | / | / | / | / |
| Zn(acac)$_2$ | 5 | / | 82-18 | 83-17 | 85-15 |
| Zn(acac)$_2$ | 5 | 92-8 | 94-6 | 94-6 | 93-7 |
| LiCl | 5 | | | | |

The foregoing description of the invention are set forth only by means of illustration. As will be readily apparent to those skilled in the art, other variations and modifications can readily be employed without departing from the spirit and scope of the invention, which is described above and embodied in the following claims.

The invention claimed is:

1. A process for the transesterification of an ester of a carboxylic or a carbonic acid, comprising reacting the ester of the carboxylic or carbonic acid with an alcohol in the presence of a catalyst consisting of a mixture of a metal 1,3-dicarbonyl complex with an inorganic salt, wherein the metal 1,3-dicarbonyl complex consists of metal acetylacetonates represented by formula

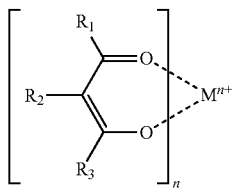

wherein n=1, 2 or 3; $R_1$ is C1-C4 alkyl, phenyl or substituted phenyl; $R_2$ is hydrogen, C1-C4 alkyl, phenyl or substituted phenyl; $R_3$ is C1-C4 alkyl, phenyl or substituted phenyl; and M represents a metal cation selected from the group consisting of lithium, zinc and iron.

2. The process according to claim 1, wherein the carboxylic acid ester is represented by the formula RCOOR', wherein R is the saturated or unsaturated aliphatic or aromatic residue of said carboxylic acid and wherein R' is an alkyl, cycloalkyl, aryl, aralkyl or alkaryl; or wherein R and R' taken together with the atoms to which they are attached are part of a ring; and wherein the carboxylic acid ester is reacted with an alcohol of the formula R"OH, wherein R" is alkyl optionally substituted with one or more substituents independently selected from the group consisting of hydroxy, amino, halo, alkenyl, mono- or di-alkyl-amino, sulfonate group, tetraalkyl ammonium, cyano, alkylthio, and heterocycles including saturated, unsaturated and partially saturated heterocycles; alkoxyalkyl; alkylpolyalkoxyalkyl; alkylphenoxyalkyl, alkylpolyphenoxyalkyl; phenylalkyl; alkylphenylalkyl; alkylmorpholinoalkyl; alkylpiperidinoalkyl; haloalkyl; cyanoalkyl; alkylthioalkyl; alkylimidazolidinones; mono- or di-alkyl-aminoalkyl; oxazolidines; or hydroxy alkyl.

3. The process according to claim 1, wherein the carbonic acid ester is represented by the formula ROCOOR', where R and R' are each independently alkyl, cycloalkyl, aryl, aralkyl or alkaryl; and wherein the carbonic acid ester is reacted with an alcohol of the formula R"OH wherein R" is alkyl optionally substituted with one or more substituents independently selected from the group consisting of hydroxy, amino, halo, alkenyl, mono- or di-alkyl-amino, sulfonate group, tetraalkyl ammonium, cyano, alkylthio, and heterocycles including saturated, unsaturated and partially saturated heterocycles; alkoxyalkyl; alkyl polyalkoxyalkyl; alkylphenoxyalkyl, alkylpolyphenoxyalkyl; phenylalkyl; alkylphenylalkyl; alkylmorpholinoalkyl; alkylpiperidinoalkyl; haloalkyl; cyanoalkyl; alkylthioalkyl; alkylimidazolidinones; mono- or di-alkyl-aminoalkyl; oxazolidines; or hydroxy alkyl.

4. The process according to claim 2, wherein R" is alkyl; substituted alkyl; cycloalkyl; alkoxyalkyl; alkylpolyalkoxyalkyl; alkylphenoxyalkyl; alkylpolyphenoxyalkyl; phenylalkyl; alkylphenylalkyl; alkylmorpholinoalkyl; alkylpiperidinoalkyl; haloalkyl; cyanoalkyl; alkylthioalkyl; alkylimidazolidinones; mono- or di-alkyl-aminoalkyl; alkyl oxazolidines; hydroxy alkyl, hydroxybutyl; and alkyls derived from ethylene glycol, butanediol, and polyoxyethyleneols.

5. The process according to claim 1 wherein the alcohol (R"OH) is selected from the group consisting of butanol, pentanol, isodecyl, lauryl, cetyl, stearyl, alkyl ether of polyoxyethylene, dimethylaminoethanol, 2-N-oxazolidinyl) ethyl, 2-(N-morpholino)ethyl, and dicyclopentenyloxyethyl.

6. The process of claim 1 wherein the salt contains an inorganic cation selected from the group consisting of $Zn^{2+}$, $Li^+$, $Na^+$, and $NH_4^+$.

7. The process according to claim 1, wherein the catalyst consists of a mixture of a Zn Li, or Fe 1,3-dicarbonyl complex with an inorganic salt with a respective mol ratio of 1:20 to 10:1.

8. The process according to claim 1, wherein the mole ratio of the catalyst to the alcohol is in the range of from about 0.0001 to about 0.10:1.

9. The process of claim 1 wherein n=1, 2 or 3; $R^1$ and $R^3$ are each independently C1-C4 alkyl or phenyl; and $R^2$ is hydrogen, C1-C4 alkyl, phenyl or substituted phenyl.

10. The process of claim 1 wherein the salt contains an inorganic anion selected from the group consisting of $Cl^-$, $Br^-$, and $I^-$.

* * * * *

UNITED STATES PATENT AND TRADEMARK OFFICE
CERTIFICATE OF CORRECTION

| | | |
|---|---|---|
| PATENT NO. | : 8,865,931 B2 | Page 1 of 2 |
| APPLICATION NO. | : 13/704057 | |
| DATED | : October 21, 2014 | |
| INVENTOR(S) | : Goossens et al. | |

It is certified that error appears in the above-identified patent and that said Letters Patent is hereby corrected as shown below:

On the title page,

Item [75]  "Thomas Peter Anne Goossens, Ostend (BE);
Freed Annie Camiel Vrielynck, Beernem (BE);
Noel Gabriel Cornelius Hosten, Bruges (BE);
Koen Jeanne Alfons Van Aken, Kuurne (BE)"

should read

--Thomas Peter Anne Goossens, Ostend (BE);
Freed Annie Camiel Vrielynck, Beernem (BE);
Noel Gabriel Cornelius Hosten, Brugge (BE);
Koen Jeanne Alfons Van Aken, Kuurne (BE)--;

Item (57) "This invention is directed to a process for the production of a variety of esters, particularly acrylate and methacrylate-based esters, by a transesterification reaction. This objective is achieved by reaction of an ester of a carboxylic or a carbonic acid, in particular of a saturated or unsaturated, typically, a 3 to 4 carbon atom carboxylic acid; with an alcohol in the presence of a catalyst comprising the combination of a metal 1,3-dicarbonyl complex (pref. Zn or Fe acetylacetonate) and a salt, in particular an inorganic salt, pref. ZnC12, LiCl, NaCl, NH4Cl or Lil. These catalysts are prepared from readily available starting materials within the reaction medium without the need for isolation (in-situ preparation)."

should read

(57) --Abstract: This invention is directed to a process for the production of a variety of esters, particularly acrylate and methacrylate-based esters, by a transesterification reaction. This objective is achieved by reaction of an ester of a carboxylic or a carbonic acid, in particular of a saturated or unsaturated, typically, a 3 to 4 carbon atom carboxylic acid; with an alcohol in the presence of a Signed and Sealed this
Twenty-fourth Day of May, 2016

Michelle K. Lee
*Director of the United States Patent and Trademark Office* catalyst comprising the combination of a metal 1,3-dicarbonyl complex (pref. Zn or Fe acetylacetonate) and a salt, in particular an inorganic salt, pref. $ZnCl_2$, LiCl, NaCl, $NH_4Cl$ or LiI. These catalysts are prepared from readily available starting materials within the reaction medium without the need for isolation (in-situ preparation).--;

In the specification,

Col. 1, Line 57,
"Therefore, catalyst should by continuously added to the reac-" should read
--Therefore, catalyst should be continuously added to the reac- --;

Col. 2, Line 46,
"the preparation of higher alkyl(meth)acrcylate esters starting" should read
--the preparation of higher alkyl(meth)acrylate esters starting--;

Col. 6, Line 19,
"inorganic or organic anion, i.e. $X^{p-}$ having p⁻ as a charge (i.e." should read
--inorganic or organic anion, i.e. $X^{p-}$ having $^{p-}$ as a charge (i.e.--;

Col. 6, Line 38,
"in particular about 1.25 mol %, about Larger amounts of" should read
--in particular about 1.25 mol %. Larger amounts of--;

Col. 6, Line 48,
"The initial mole ratio of saturated, aromatic, unsaturated" should read
--The initial mol ratio of saturated, aromatic, unsaturated--;

Col. 8, Line 36,
"ized in that it consists of a the combination of a metal 1,3-" should read
--ized in that it consists of the combination of a metal 1,3- --; and Col. 9, Table 1, Lines 47 and 49,
Col. 10, Table 3, Lines 31, 33 and 37,
Col. 11, Table 5, Lines 43 and 45,
Col. 12, Table 6, Line 23, 25 and 30,
"LiI" should read --LiI--.